United States Patent [19]

Levine et al.

[11] 4,309,262
[45] Jan. 5, 1982

[54] HYDRAZINE ANALYZER

[75] Inventors: Melvin Levine, New York, N.Y.; Paul J. Jacobetz, Harrison; Elmer A. Sperry, III, Pompton Plains, both of N.J.

[73] Assignee: Beckman Instruments, Inc., Fullerton, Calif.

[21] Appl. No.: 757,704

[22] Filed: Jan. 7, 1977

[51] Int. Cl.³ .................... G01N 27/28; G01N 27/46
[52] U.S. Cl. .................. 204/195 R; 204/1 T
[58] Field of Search ............... 204/195 R, 1 N

[56] References Cited

U.S. PATENT DOCUMENTS

| | | | |
|---|---|---|---|
| 2,651,612 | 9/1953 | Haller | 204/195 R |
| 2,851,654 | 9/1958 | Haddad | 204/195 R |
| 3,214,354 | 10/1965 | Capliano et al. | 204/195 R |
| 3,315,270 | 4/1967 | Hersch | 204/1 B |
| 3,432,403 | 3/1969 | Glass et al. | 204/195 R |
| 3,575,835 | 4/1971 | Smith et al. | 204/195 R |
| 3,694,338 | 9/1972 | Weingarten | 204/195 R |
| 3,972,792 | 8/1976 | Layen | 204/195 R |
| 4,002,547 | 1/1977 | Neti et al. | 204/195 F |

*Primary Examiner*—G. L. Kaplan
*Attorney, Agent, or Firm*—Robert J. Steinmeyer; Paul R. Harder

[57] ABSTRACT

An improved hydrazine analyzer is disclosed wherein sample and electrolyte solutions are supplied from constant flow rate sources into a mixing chamber where they are premixed. The premixed combination of electrolyte and sample is then passed through a sensing chamber having a sensing thimble disposed therein. The thimble is of a porous material having a platinum wire electrode wound about the outside thereof and having a silver wire inserted into silver chloride salt on the inside thereof to form a reference half cell. As the electrolyte-sample mixture passes through the sensing chamber, a portion of the fluid passes from the outside of the thimble to the inside of the thimble wetting the silver chloride salt to establish electrical contact and provide the internal filling solution of the reference half cell.

2 Claims, 2 Drawing Figures

HYDRAZINE ANALYZER

BACKGROUND OF THE INVENTION

The present invention relates to hydrazine analyzers and more particularly to hydrazine analyzers wherein the hydrazine is measured by utilizing its tendency to create an electrochemical reaction with a platinum wire under oxidizing conditions.

Hydrazine is added to boiler feed water to improve the life and operation of the equipment by controlling dissolved oxygen concentration. Thus, it is desirable to have reliable equipment capable of accurately detecting the quantity of hydrazine present in the feed water at any particular time. Preferably, the hydrazine is detected on a continuing basis so that the measurement can be used as the input to a feedback loop controlling the rate at which hydrazine is injected into the feed water. Typical prior art devices used for this purpose are shown in the U.S. Pat. Nos. to Haller (2,651,612), and Weingarten (3,694,338). Such prior devices for the detection of hydrazine have generally embodied an elongated, porous, closed end tube having a noble metal electrode (typically of platinum) wound about the outer surface, a silver inner electrode extending into the porous tube which has been filled with a silver oxide or silver chloride salt, and means for feeding an electrolyte into the tube. The electrolyte in combination with the salt creates an internal filling solution forming a half cell on the interior of the tube. The electrolyte solution further passes from the inside of the porous tube through to the outside thereof to contact the external metal electrode. With this arrangement, a gas or liquid containing hydrazine contacting the external electrode produces an electrochemical reaction which causes a voltage to be developed between the electrodes proportional to the quantity of hydrazine present. This voltage can then be detected and displayed by a suitable indicator. Since the salt in the porous tube is generally in the form of a powder poured into the tube and about the silver electrode, the life of the cell is limited to the time elapsed until the salt has washed out of the tube so that the required internal filling solution for the reference half cell is no longer present. The cell then has to be discarded or refilled, if possible. In order to prevent this, the patent to Weingarten teaches that it is desirable to insert the internal half cell within a separate porous enclosure contained within or in close adjacent communicating relationship with the inside of the porous tube.

In all cases, however, the interface between the electrolyte, sample solution, and platinum electrode only occurs at the surface of the porous tube having the platinum outer electrode wound thereon. Flow rates of the sample past the electrode, flow rate of the electrolyte solution from the inside of the tube to the external surface thereof, and the like, are critical factors in the electrochemical reaction taking place at the surface of the porous tube. For example, if the flow rate of the sample does not create a washing of the surface of the tube as in the case when there is no flow, a layer of electrolyte or previously reacted sample can build up surrounding the electrode at the surface of the tube wherein the sample is no longer in contact with the electrode and no, or a reduced, electrochemical reaction is thereby caused to take place. Likewise, if insufficient electrolyte is present at the surface of the porous tube, no, or a reduced, electrochemical reaction is thereby caused to take place.

Therefore, it is the object of the present invention to provide an improved hydrazine analyzer of the general type described wherein the loss of salt from the reference half cell is virtually eliminated and constant conditions for sample-electrolyte interaction with the platinum electrode are present.

SUMMARY OF THE INVENTION

The foregoing objective has been achieved by the present invention wherein the electrolyte and sample are premixed in optimum proportions and immediately passed through a sensing chamber to contact the noble metal external electrode. The external electrode is wound about a porous, closed end tube extending into the sensing chamber and having a silver wire inserted therein in the presence of a salt such as a mixture of silver chloride. A portion of the electrolyte-sample mixture solution saturates the porous tube and the salt therein to create the internal filling solution and, additionally, establish electrical contact with the internal half cell. Since the electrolyte is already present at the surface of the porous tube, it is not necessary for electrolyte to pass from the interior to the exterior and, therefore, a microporous tube can be used wherein substantially no flow of liquid takes place therethrough and only electrical contact is maintained. The electrolyte may be a buffered solution which, by mixing with the sample, maintains the pH of the mixture constant thereby preventing changes in the instrument output which normally attend changes in sample pH. Since an electrochemical reaction will occur whenever hydrazine contacts the platinum electrode under oxidizing conditions, maintaining the pH substantially constant at a preferred pH of 9 makes the resultant electrochemical reaction relative to the reference half cell a function of the hydrazine concentration as desired. Since there is virtually no flow of electrolyte from the interior of the porous tube to the exterior, there is no change in instrument output related to changes in flow through the tube which could be caused by salt blocking the pores of the tube.

DESCRIPTION OF THE PREFERRED EMBODIMENT

Figure 1:
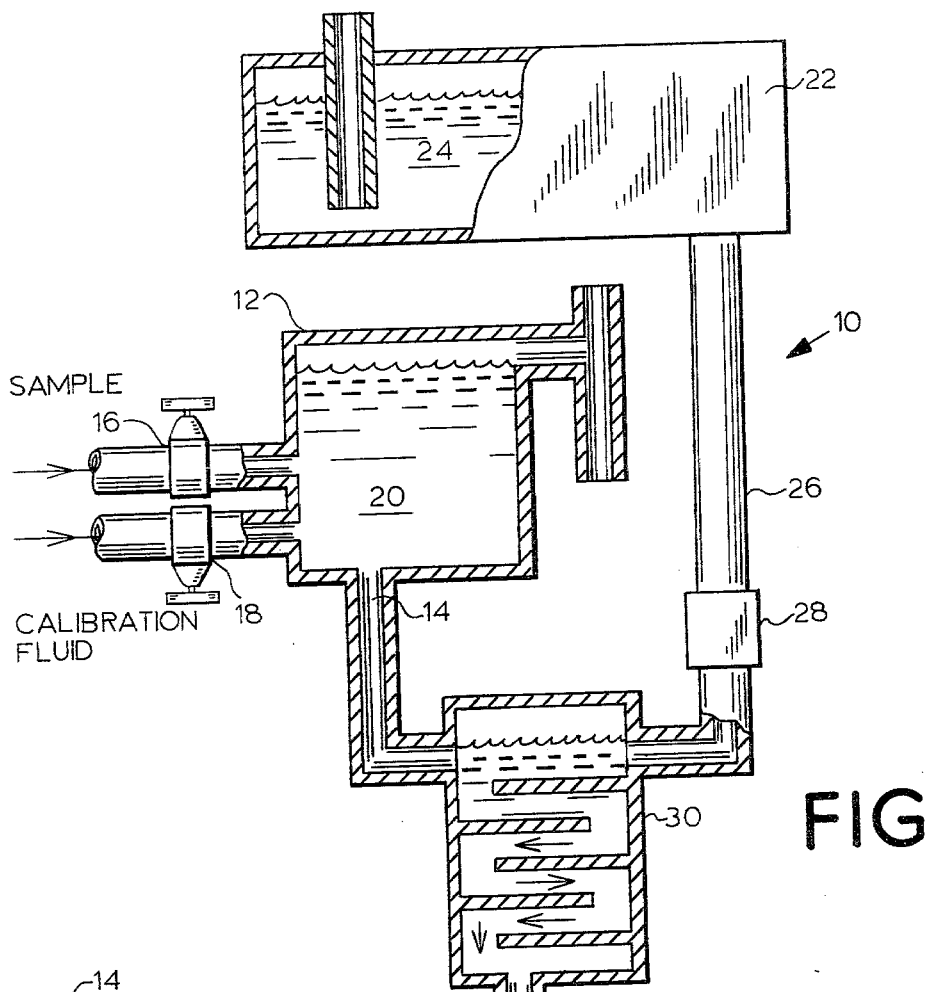
FIG. 1 is a simplified drawing, in partially cutaway form, depicting the basic elements and mode of operation of the present invention.

The basic elements comprising the present invention are shown in FIG. 1. It is to be understood that this is a simplified drawing representing the elements of the system only and is not intended to be to scale. The hydrazine analyzer system of the present invention is generally indicated as 10 and comprises a first container 12 adapted to hold a fluid so as to provide a constant head pressure at the output line 14 thereof. In the preferred embodiment, first container 12 is adapted to be connected either to a source of sample or calibration fluid through valves 16 and 18 respectively. For purposes of example, it is to be assumed that valve 18 is closed and valve 16 is open such that first container 12 contains sample designated as 20.

Figure 2:
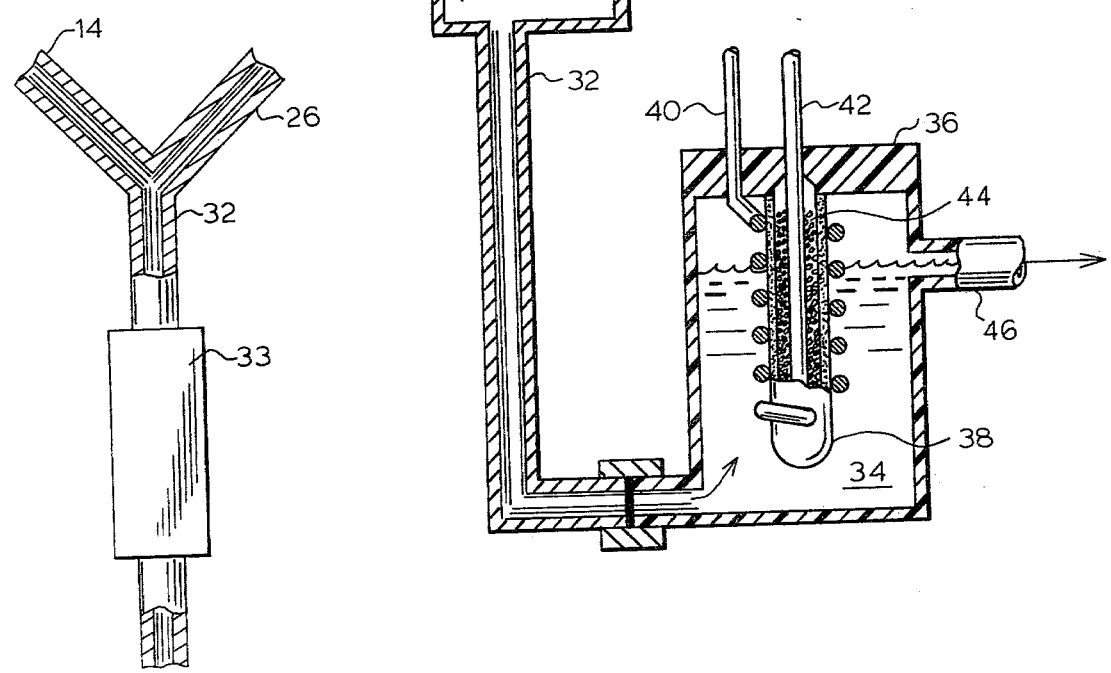
FIG. 2 is a simplified drawing of an alternate means for mixing the electrolyte and sample according to the present invention including sample flow control means.

A second container 22 is provided wherein electrolyte designated as 24 is stored. The preferred electrolyte is a buffer solution the concentration thereof as employed in a tested embodiment of the present invention comprising a mixture of 5 parts 0.025 molar sodium borate decahydrate ($Na_2B_4O_7.10H_2O$) to 1 part 0.1 molar boric acid ($H_3BO_3$). The output line 26 of second container 22 has flow indication and control means 28 provided in line therewith according to any of many techniques well known in the art whereby the flow rate of electrolyte 24 through output line 26 can be controlled. Output line 14 from first container 12 and output line 26 from second container 22 are connected as inputs to a baffled mixing chamber 30. Baffled mixing chamber 30 can be of any appropriate construction such as that illustrated wherein the two fluids being input thereto are thoroughly mixed upon entry into output line 32 thereof. Thus, an electrolyte-sample mixture designated 34 is present in output line 32. By controlling the flow of electrolyte 24 using flow control means 28, a desired optimum electrolyte-sample mixture 34 can be produced in output line 32. It has been found that, when employing the preferred buffer solution electrolyte 24 described above, an electrolyte flow rate of 0.1 milliliters per minute and a sample flow rate of 70 milliliters per minute giving an electrolyte to sample ratio of 1 to 700 provides optimum results. The alternate configuration of FIG. 2 has also been found to work well and, in fact, may give superior results depending on the exact configuration of the apparatus built. In the apparatus of FIG. 2, lines 14 and 26 are joined as with a "Y" to form line 32. A mechanical type flowmeter 33 is then inserted in line 32 in lieu of mixing chamber 30 to thoroughly mix the electrolyte and sample while, additionally, providing flow control and indication.

The output line 32 containing the electrolyte-sample mixture 34 is connected as an input to a sensing chamber 36. A porous, closed end tube or thimble 38 is contained within sensing chamber 36. Thimble 38 has a platinum wire electrode 40 wound about the external surface thereof and passing out of sensing chamber 36 for external connection thereto. A silver electrode 42 is disposed within the thimble 38 and also passes to the exterior of sensing chamber 36 for electrical connection thereto. A quantity of salt 44, with silver chloride being preferred, is disposed within thimble 38 in contact with the silver electrode 42. An outlet 46 is provided in sensing chamber 36 such that the electrolyte-sample mixture 34 entering sensing chamber 36 will be caused to pass across thimble 38 contacting platinum electrode 40 before exiting from sensing chamber 36 through the outlet 46. Thimble 38 is preferably constructed of a microporous material selected from a number of such material well known to those skilled in the art such that the electrolyte-sample mixture 34 will pass therethrough from the exterior to the interior so as to saturate the salt 44 to provide the internal filling solution and, additionally, establish electrical contact through the thimble 38 to the internal reference half cell formed by silver electrode 42 and saturated salt 44 while preventing the salt 44 from passing from the interior to the exterior.

While the preferred embodiment as hereinbefore described employs a platinum electrode 40 wound about a porous thimble 38 having the reference half cell inside, it is to be understood that the novel approach of premixing the electrolyte and sample allows for variations within the placement of electrode 40 and the reference half cell comprising electrode 42 and salt 44. As one alternate approach, the electrode 40 need not be directly wound on the thimble 38 in order to be adjacent the source of electrolyte. Likewise, the thimble need not be of a porous material. As an alternative, a material such as that employed in reference electrodes manufactured by the assignee of this application, Beckman Instruments, Inc., and sold under the trademark LAZARAN can be employed to advantage. Such non-porous material provides for electrical conductivity without fluid flow therethrough. In such case, the internal filling solution would have to be provided in the internal reference half cell since the sample-electrolyte solution could not pass through the thimble walls to provide the internal filling solution.

When constructed as shown and employing the flow rates and concentrations previously described, a tested embodiment of the present invention regularly measured concentrations in the range of from 0 to 100 parts per billion hydrazine, but concentrations of up to 1000 parts per billion can be measured. The system 10 as built and tested typically had an electrical output measured across the electrodes 40 and 42 of approximately 0.5 microamperes per part per billion hydrazine employing a 5000 ohm load.

Having thus described our invention, we claim:

1. Apparatus for measuring the hydrazine content in a system having a source of a sample stream and a source of electrolyte, said apparatus comprising:
   mixing means connected to the electrolyte source and the sample stream source for mixing said sample stream and said electrolyte to form a sample mixture;
   chamber means for receiving said sample mixture;
   porous closed end tube disposed within said chamber means for permitting flow of said sample mixture therethrough;
   noble metal electrode configured around said porous closed end tube; and
   dry reference half cell selected from the group consisting of silver-silver oxide and silver-silver chloride disposed within said porous closed end tube to permit saturation of said dry half cell when said sample mixture flows through said porous closed end tube to establish electrical contact between said noble metal electrode and the electrode of said dry reference half cell.

2. The apparatus as claimed in claim 1 wherein:
   the nobel metal electrode is platinum.

* * * * *